(12) United States Patent
Peterson

(10) Patent No.: US 11,662,281 B2
(45) Date of Patent: May 30, 2023

(54) COMPOSITIONS AND METHODS FOR BIOLOGICAL SAMPLE PROCESSING

(71) Applicant: Gen-Probe Incorporated

(72) Inventor: Patrick Lynn Peterson, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 278 days.

(21) Appl. No.: 16/769,227

(22) PCT Filed: Dec. 12, 2018

(86) PCT No.: PCT/US2018/065105
§ 371 (c)(1),
(2) Date: Jun. 2, 2020

(87) PCT Pub. No.: WO2019/118550
PCT Pub. Date: Jun. 20, 2019

(65) Prior Publication Data
US 2020/0400537 A1 Dec. 24, 2020

Related U.S. Application Data

(60) Provisional application No. 62/598,207, filed on Dec. 13, 2017.

(51) Int. Cl.
*G01N 1/40* (2006.01)
*C12N 15/10* (2006.01)
*G01N 1/34* (2006.01)
*G01N 1/00* (2006.01)

(52) U.S. Cl.
CPC ....... *G01N 1/4055* (2013.01); *C12N 15/1003* (2013.01); *G01N 1/34* (2013.01); *G01N 2001/002* (2013.01); *G01N 2001/4083* (2013.01)

(58) Field of Classification Search
CPC .... C12N 15/1003; G01N 1/34; G01N 1/4055; G01N 2001/002; G01N 2001/4083
See application file for complete search history.

(56) References Cited

U.S. PATENT DOCUMENTS

| 5,837,452 A * | 11/1998 | Clark ................ C12N 1/06 424/9.1 |
| 2002/0001539 A1 | 1/2002 | DiCesare et al. |
| 2006/0142668 A1 | 6/2006 | Triva |
| 2008/0300397 A1 | 12/2008 | Kenrick et al. |
| 2012/0171712 A1 | 7/2012 | Triva |
| 2017/0038370 A1 | 2/2017 | Zourob |

FOREIGN PATENT DOCUMENTS

WO 2017033099 A1 3/2017

OTHER PUBLICATIONS

PCT, Search Report and Written Opinion, International Application No. PCT/US2018/065105, dated Mar. 20, 2019, 11 pages.

* cited by examiner

*Primary Examiner* — Christine T Mui
*Assistant Examiner* — Kathryn Elizabeth Limbaugh
(74) *Attorney, Agent, or Firm* — Adam M. Breier; Michael J. Gilly

(57) ABSTRACT

Methods, apparatuses, and systems are provided for processing a biological sample. Exemplary methods comprise transferring a swab associated with an aliquot of the biological sample into a wash liquid, wherein a first portion of the aliquot is released into the wash liquid; and transferring the swab into a carrier liquid, wherein a second portion of the aliquot is released into the carrier liquid. The methods can provide efficient transfer of analyte such as cells or nucleic acid into the carrier liquid while releasing particulate matter, viscous polymers, or other undesired material into the wash liquid. Alternatively or in addition, the methods can also release desired material into the wash liquid, e.g., cells, which can be used in applications such as culturing.

20 Claims, No Drawings

COMPOSITIONS AND METHODS FOR BIOLOGICAL SAMPLE PROCESSING

CROSS-REFERENCE TO RELATED APPLICATIONS

This application is a national stage entry under 35 U.S.C. § 371 of International Patent Application No. PCT/US2018/065105, filed Dec. 12, 2018, which claims the benefit under 35 U.S.C. § 119(e) of U.S. Provisional Application No. 62/598,207, filed Dec. 13, 2017, the disclosure of which is hereby incorporated by reference in its entirety.

TECHNICAL FIELD

This disclosure relates to the field of biotechnology. More particularly, the disclosure concerns methods and compositions for processing biological samples, for example in preparation for use in subsequent analytical procedures.

BACKGROUND

Many molecular biology procedures such as in vitro amplification and in vitro hybridization of nucleic acids include some preparation of nucleic acids to facilitate the subsequent procedure. Methods of nucleic acid purification may isolate all nucleic acids present in a sample, isolate different types of nucleic acids based on physical characteristics, or isolate specific nucleic acids from a sample. Many methods involve complicated procedures, use harsh chemicals or conditions, or require a long time to complete the nucleic acid isolation. Some methods involve use of specialized oligonucleotides, each specific for an intended target nucleic acid which adds complexity to the design, optimization and performance of methods, particularly if isolation of more than one target nucleic acid is desired or if the sequence of the desired target nucleic acid is unknown. Some methods isolate target nucleic acids without requiring a particular target sequence but do not isolate all sequences efficiently.

Thus, there remains a need for a simple, efficient, and fast method to separate nucleic acids of interest from other sample components, and for apparatuses and systems that perform such methods.

SUMMARY OF THE DISCLOSURE

Embodiment 1 is a method of processing a biological sample, the method comprising: a) transferring a swab associated with an aliquot of the biological sample into a wash liquid, wherein a first portion of the aliquot is released into the wash liquid; and b) transferring the swab into a carrier liquid, wherein a second portion of the aliquot is released into the carrier liquid.

Embodiment 2 is the method of embodiment 1, wherein the biological sample is a suspension.

Embodiment 3 is the method of any one of the preceding embodiments, wherein the biological sample comprises particulate matter.

Embodiment 4 is the method of embodiment 3, wherein the first portion of the aliquot comprises a greater amount of particulate matter than does the second portion.

Embodiment 5 is the method of any one of the preceding embodiments, wherein the biological sample comprises at least one viscous polymer.

Embodiment 6 is the method of embodiment 5, wherein the first portion of the aliquot comprises a greater amount of viscous polymer than does the second portion.

Embodiment 7 is the method of any one of embodiments 5 to 6, wherein the at least one viscous polymer includes a polysaccharide.

Embodiment 8 is the method of any one of embodiments 5 to 7, wherein the at least one viscous polymer includes an extracellular nucleic acid.

Embodiment 9 is the method of any one of the preceding embodiments, wherein the biological sample comprises a lipid.

Embodiment 10 is the method of any one of the preceding embodiments, wherein the biological sample comprises a lipid phase or a lipid emulsion.

Embodiment 11 is the method of any one of the preceding embodiments, wherein the biological sample comprises stool.

Embodiment 12 is the method of any one of the preceding embodiments, wherein the biological sample comprises sputum, mucus, blood, soil, sludge, or a microbial growth.

Embodiment 13 is the method of any one of the preceding embodiments, wherein the biological sample is of plant or animal origin.

Embodiment 14 is the method of any one of the preceding embodiments, wherein the biological sample is of mammalian origin.

Embodiment 15 is the method of any one of the preceding embodiments, wherein the biological sample is of human origin.

Embodiment 16 is the method of any one of the preceding embodiments, wherein the biological sample is obtained from a food.

Embodiment 17 is the method of any one of the preceding embodiments, wherein the swab undergoes agitation in the wash liquid to release the first portion of the aliquot into the wash liquid.

Embodiment 18 is the method of embodiment 17, wherein the agitation in the wash liquid comprises swirling, stirring, or rotating the swab in the wash liquid.

Embodiment 19 is the method of embodiment 17 or 18, wherein the wash liquid is contained in a vessel and the agitation in the wash liquid further comprises pressing the swab against a wall of the vessel during at least part of the swirling, stirring, or rotating.

Embodiment 20 is the method of any one of embodiments 17 to 19, wherein the agitation in the wash liquid comprises vortexing the swab in the wash liquid.

Embodiment 21 is the method of any one of embodiments 17 to 20, wherein the agitation in the wash liquid is performed for a period of 0.5 to 15 seconds.

Embodiment 22 is the method of embodiment 21, wherein the agitation in the wash liquid is performed for a period of 0.5 to 2 seconds, 2 to 4 seconds, 4 to 6 seconds, 6 to 8 seconds, 8 to 10 seconds, 10 to 12 seconds, or 12 to 15 seconds.

Embodiment 23 is the method of any one of the preceding embodiments, wherein the swab undergoes agitation in the carrier liquid to release the second portion of the aliquot into the carrier liquid.

Embodiment 24 is the method of embodiment 23, wherein the agitation in the carrier liquid comprises swirling, stirring, or rotating the swab in the carrier liquid.

Embodiment 25 is the method of embodiment 23 or 24, wherein the carrier liquid is contained in a vessel and the agitation in the carrier liquid further comprises pressing the swab against a wall of the vessel during at least part of the swirling, stirring, or rotating.

Embodiment 26 is the method of any one of embodiments 23 to 25, wherein the agitation in the carrier liquid comprises vortexing the carrier liquid.

Embodiment 27 is the method of any one of embodiments 23 to 26, wherein the agitation in the carrier liquid is performed for a period of 0.5 to 15 seconds.

Embodiment 28 is the method of embodiment 27, wherein the agitation in the carrier liquid is performed for a period of 0.5 to 2 seconds, 2 to 4 seconds, 4 to 6 seconds, 6 to 8 seconds, 8 to 10 seconds, 10 to 12 seconds, or 12 to 15 seconds.

Embodiment 29 is the method of any one of the preceding embodiments, wherein the swab comprises a tip and the tip comprises flocked fibers.

Embodiment 30 is the method of any one of the preceding embodiments, wherein the swab comprises a tip and the tip comprises wrapped fibers.

Embodiment 31 is the method of embodiment 29 or 30, wherein the flocked or wrapped fibers comprise a hydrophilic polymer.

Embodiment 32 is the method of any one of embodiments 29 to 31, wherein the flocked or wrapped fibers comprise rayon, polyester, polyamide, carbon fiber, alginate, cotton, silk, or a mixture of two or more thereof.

Embodiment 33 is the method of any one of embodiments 29 to 32, wherein the flocked or wrapped fibers comprise polyester.

Embodiment 34 is the method of any one of embodiments 29 to 33, wherein the flocked or wrapped fibers comprise polyamide.

Embodiment 35 is the method of any one of embodiments 29 to 34, wherein the flocked or wrapped fibers comprise cotton.

Embodiment 36 is the method of any one of embodiments 29 to 35, wherein the flocked or wrapped fibers have a thickness of 0.5 to 3 mm.

Embodiment 37 is the method of any one of embodiments 29 to 36, wherein the flocked or wrapped fibers have a linear density of 1 to 4 mg per 10 meters.

Embodiment 38 is the method of any one of embodiments 29 to 37, wherein the flocked or wrapped fibers have a linear density of 1 to 1.5, 1.5 to 2, 2 to 2.5, 2.5 to 3, 3 to 3.5, or 3.5 to 4 Dtex.

Embodiment 39 is the method of any one of embodiments 29 to 38, wherein the flocked or wrapped fibers are associated with a surfactant.

Embodiment 40 is the method of embodiment 39, wherein the surfactant is cationic.

Embodiment 41 is the method of embodiment 39 or 40, wherein the surfactant comprises a quaternary amine.

Embodiment 42 is the method of any one of embodiments 39 to 41, wherein the surfactant comprises benzalkonium.

Embodiment 43 is the method of any one of embodiments 39 to 42, wherein the surfactant comprises chloride.

Embodiment 44 is the method of any one of the preceding embodiments, wherein the swab becomes associated with a volume of 1 to 500 microliters of the biological sample in step (a).

Embodiment 45 is the method of embodiment 44, wherein the swab becomes associated with a volume of 1 to 5, 5 to 10, 10 to 20, 20 to 50, 50 to 100, 100 to 150, 150 to 200, 200 to 250, 250 to 300, 300 to 350, or 350 to 500 microliters of the biological sample in step (a).

Embodiment 46 is the method of embodiment 44, wherein the swab becomes associated with a volume of 1 to 3, 3 to 8, 8 to 15, 15 to 20, 20 to 75, 75 to 125, 125 to 175, 175 to 225, 225 to 275, 275 to 325, 325 to 375, or 375 to 500 microliters of the biological sample in step (a).

Embodiment 47 is the method of any one of the preceding embodiments, wherein the biological sample comprises or is suspected of comprising at least one cell.

Embodiment 48 is the method of any one of the preceding embodiments, wherein the biological sample comprises or is suspected of comprising at least one bacterium.

Embodiment 49 is the method of any one of the preceding embodiments, wherein the biological sample comprises or is suspected of comprising at least one spore.

Embodiment 50 is the method of embodiment 48 or 49, wherein the bacterium or spore is a *Clostridium*.

Embodiment 51 is the method of embodiment 48 or 49, wherein the bacterium or spore is *Clostridium difficile*.

Embodiment 52 is the method of embodiment 48, wherein the bacterium is a *Staphylococcus*.

Embodiment 53 is the method of embodiment 48, wherein the bacterium is MRSA.

Embodiment 54 is the method of any one of the preceding embodiments, wherein the biological sample comprises or is suspected of comprising at least one virus.

Embodiment 55 is the method of embodiment 54, wherein the virus is norovirus.

Embodiment 56 is the method of any one of the preceding embodiments, wherein the biological sample comprises or is suspected of comprising at least one pathogen.

Embodiment 57 is the method of embodiment 56, wherein the pathogen is a gastrointestinal pathogen.

Embodiment 58 is the method of any one of embodiments 47 to 57, wherein the at least one cell, bacterium, virus, or pathogen includes one or more of a *Campylobacter*, a *Plesiomonas*, a *Salmonella*, a *Vibrio*, a *Yersinia*, an *E. coli*, a *Shigella*, a *Cryptosporidium*, a *Cyclospora*, an *Entamoeba*, an Adenovirus, a Rotavirus, or a Sapovirus.

Embodiment 59 is the method of embodiment 58, wherein the at least one cell, bacterium, virus, or pathogen includes one or more of *Campylobacter jejuni, Campylobacter coli, Campylobacter upsaliensis, Plesiomonas shigelloides, Salmonella typhimurium, Vibrio cholerae, Vibrio vulnificus, Vibrio parahemolyticus, Yersinia pestis*, enteroaggregative *E. coli*, enteroinvasive *E. coli*, enterotoxigenic *E. coli*, *E. coli* O157, *Shigella flexneri, Cryptosporidium parvum, Cyclospora cayetanensis, Entamoeba histolytica*, Adenovirus serotype 40 or 41, Rotavirus A, or Sapporo virus.

Embodiment 60 is the method of any one of the preceding embodiments, wherein the wash liquid is aqueous.

Embodiment 61 is the method of embodiment 60, wherein the wash liquid is water.

Embodiment 62 is the method of embodiment 60, wherein the wash liquid comprises a buffer.

Embodiment 63 is the method of embodiment 60, wherein the wash liquid has a pH of 3 to 11.

Embodiment 64 is the method of embodiment 63, wherein the wash liquid has a pH of 3 to 4, 4 to 5, 5 to 6, 6 to 7, 7 to 8, 8 to 9, 9 to 10, or 10 to 11.

Embodiment 65 is the method of embodiment 63, wherein the wash liquid has a pH of 3.5 to 4.5, 4.5 to 5.5, 5.5 to 6.5, 6.5 to 7.5, 7.5 to 8.5, 8.5 to 9.5, or 9.5 to 10.5.

Embodiment 66 is the method of any one of the preceding embodiments, wherein the wash liquid comprises a salt.

Embodiment 67 is the method of any one of the preceding embodiments, wherein the wash liquid comprises a detergent.

Embodiment 68 is the method of embodiment 67, wherein the detergent is anionic.

Embodiment 69 is the method of embodiment 67, wherein the detergent is nonionic or zwitterionic.

Embodiment 70 is the method of any one of the preceding embodiments, wherein the wash liquid has an osmolarity of 0 to 1000 mOsm.

Embodiment 71 is the method of embodiment 69, wherein the wash liquid has an osmolarity of 0 to 50 mOsm, 20 to 50 mOsm, 50 to 100 mOsm, 100 to 200 mOsm, 200 to 300 mOsm, 300 to 400 mOsm, 400 to 500 mOsm, 500 to 600 mOsm, 600 to 700 mOsm, 700 to 800 mOsm, or 800 to 1000 mOsm.

Embodiment 72 is the method of any one of the preceding embodiments, wherein the wash liquid is present within a vessel and the wash liquid has a volume of 0.2 to 2 ml.

Embodiment 73 is the method of embodiment 72, wherein the wash liquid has a volume of 0.2 to 0.4 ml, 0.4 to 0.6 ml, 0.6 to 0.8 ml, 0.8 to 1 ml, 1 to 1.2 ml, 1.2 to 1.4 ml, 1.4 to 1.6 ml, 1.6 to 1.8 ml, or 1.8 to 2 ml.

Embodiment 74 is the method of any one of the preceding embodiments, wherein the carrier liquid is aqueous.

Embodiment 75 is the method of embodiment 74, wherein the carrier liquid is water.

Embodiment 76 is the method of embodiment 74, wherein the carrier liquid has a pH of 3 to 14.

Embodiment 77 is the method of embodiment 74, wherein the carrier liquid has a pH of 3 to 4, 4 to 5, 5 to 6, 6 to 7, 7 to 8, 8 to 9, 9 to 10, 10 to 11, 11 to 12, 12 to 13, or 13 to 14.

Embodiment 78 is the method of any one of the preceding embodiments, wherein the carrier liquid comprises a protease.

Embodiment 79 is the method of any one of the preceding embodiments, wherein the carrier liquid comprises an RNase inhibitor.

Embodiment 80 is the method of any one of embodiments 1 to 78, wherein the carrier liquid comprises an RNase.

Embodiment 81 is the method of any one of the preceding embodiments, wherein the carrier liquid comprises a divalent cation chelator.

Embodiment 82 is the method of any one of the preceding embodiments, wherein the carrier liquid is a lysis solution.

Embodiment 83 is the method of any one of embodiments 1 to 82, further comprising adding a lysis solution to the carrier liquid after step (b).

Embodiment 84 is the method of embodiment 82 or 83, wherein the lysis solution comprises a base.

Embodiment 85 is the method of embodiment 84, wherein the lysis solution comprises a hydroxide base.

Embodiment 86 is the method of embodiment 85, wherein the lysis solution comprises an alkali hydroxide base.

Embodiment 87 is the method of any one of embodiments 82 to 86, wherein the lysis solution has a pH of 12 to 14.

Embodiment 88 is the method of embodiment 87, wherein the lysis solution has a pH of 13 to 13.5.

Embodiment 89 is the method of any one of the preceding embodiments, wherein the carrier liquid or lysis solution comprises a detergent.

Embodiment 90 is the method of embodiment 89, wherein the detergent is anionic.

Embodiment 91 is the method of embodiment 89, wherein the detergent is an alkyl sulfate.

Embodiment 92 is the method of embodiment 91, wherein the detergent is a dodecyl sulfate.

Embodiment 93 is the method of any one of embodiments 89 to 92, wherein the detergent is a sodium salt.

Embodiment 94 is the method of any one of embodiments 89 to 92, wherein the detergent is a lithium salt.

Embodiment 95 is the method of any one of the preceding embodiments, wherein the carrier liquid is present within a vessel and the carrier liquid has a volume of 0.2 to 10 ml.

Embodiment 96 is the method of embodiment 95, wherein the carrier liquid has a volume of 0.2 to 0.4 ml, 0.4 to 0.6 ml, 0.6 to 0.8 ml, 0.8 to 1 ml, 1 to 1.2 ml, 1.2 to 1.4 ml, 1.4 to 1.6 ml, 1.6 to 1.8 ml, 1.8 to 2 ml, 2 ml to 3 ml, 3 ml to 4 ml, 4 ml to 6 ml, 6 ml to 8 ml, or 8 ml to 10 ml.

Embodiment 97 is the method of any one of the preceding embodiments, wherein the biological sample comprises cells and the method further comprises lysing cells after step (b).

Embodiment 98 is the method of any one of the preceding embodiments, wherein the biological sample comprises viruses having a coat or envelope and the method further comprises releasing nucleic acid from the coat or envelope.

Embodiment 99 is the method of any one of the preceding embodiments, wherein the biological sample comprises at least one target nucleic acid, and the method further comprises capturing the target nucleic acid with at least one capture probe or isolating the target nucleic acid by precipitation or chromatography.

Embodiment 100 is the method of embodiment 99, wherein the at least one capture probe includes at least one non-specific capture probe.

Embodiment 101 is the method of embodiment 100, wherein the at least one non-specific capture probe includes one or more of a poly-(k) or poly-(r) capture probe.

Embodiment 102 is the method of any one of the preceding embodiments, further comprising determining the presence or absence of at least one macromolecule in the second portion of the biological sample.

Embodiment 103 is the method of any one of the preceding embodiments, further comprising quantifying at least one macromolecule in the second portion of the biological sample.

Embodiment 104 is the method of embodiment 102 or 103, wherein the determining or quantifying comprises separating the at least one macromolecule from other cellular components in the second portion of the aliquot.

Embodiment 105 is the method of any one of embodiments 102 to 104, wherein the at least one macromolecule is a nucleic acid.

Embodiment 106 is the method of any one of the preceding embodiments, further comprising amplifying at least one nucleic acid from the second portion of the aliquot.

Embodiment 107 is the method of any one of the preceding embodiments, further comprising sequencing at least one nucleic acid from the second portion of the aliquot or an amplicon thereof.

Embodiment 108 is the method of any one of the preceding embodiments, further comprising hybridizing a detection probe to at least one nucleic acid from the second portion of the biological sample or an amplicon thereof.

Embodiment 109 is the method of any one of the preceding embodiments, further comprising performing an invasive cleavage assay to detect at least one nucleic acid from the second portion of the biological sample or an amplicon thereof.

Embodiment 110 is the method of any one of embodiments 102 to 104, wherein the at least one macromolecule is a polypeptide.

Embodiment 111 is the method of embodiment 110, further comprising binding an antibody to the polypeptide, binding an aptamer to the polypeptide, sequencing the polypeptide, electrophoresing the polypeptide, or analyzing the polypeptide mass spectrometrically.

Embodiment 112 is the method of any one of the preceding embodiments, wherein the biological sample is a crude sample.

Embodiment 113 is the method of any one of the preceding embodiments, further comprising contacting the biological sample with the swab, wherein the aliquot of the biological sample and the swab become associated.

Embodiment 114 is the method of any one of the preceding embodiments, wherein the first portion of the aliquot released into the wash liquid comprises cells.

Embodiment 115 is the method of embodiment 114, further comprising culturing cells that were released into the wash liquid or performing an optical analytical technique on cells that were released into the wash liquid.

Embodiment 116 is an apparatus or system configured to perform the method of any one of the preceding embodiments.

Embodiment 117 is an apparatus or system comprising a gripper for holding a swab, wherein the apparatus or system is configured to transfer a swab with which an aliquot of a biological sample is associated into a wash liquid so as to release a first portion of the aliquot into the wash liquid, and transfer the swab into a carrier liquid so as to release a second portion of the aliquot into the carrier liquid.

Embodiment 118 is the apparatus or system of embodiment 116 or 117, which is configured to contact the biological sample with the swab so as to associate the aliquot of the biological sample with the swab.

Embodiment 119 is the apparatus or system of any one of embodiments 116 to 118, wherein the gripper is a clamp, claw, ring, or gasket.

Embodiment 120 is the apparatus or system of any one of embodiments 116 to 119, wherein the apparatus is configured to agitate the swab or at least one of the wash liquid or the carrier liquid to facilitate release of at least one of the first portion into the wash liquid or the second portion into the carrier liquid.

Embodiment 121 is the apparatus or system of any one of embodiments 116 to 120, which comprises a receptacle for holding at least one container.

Embodiment 122 is the apparatus or system of embodiment 121, wherein the receptacle is a rack.

Embodiment 123 is the apparatus or system of any one of embodiments 116 to 122, wherein the apparatus or system further comprises at least one or at least two reservoirs for holding wash liquid and/or carrier liquid.

Embodiment 124 is the apparatus or system of embodiment 123, wherein the apparatus or system further comprises tubing for transporting at least one of wash liquid or carrier liquid from the reservoir(s) into at least one container.

Embodiment 125 is the apparatus or system of any one of embodiments 117 to 124, which is configured to perform the method of any one of embodiments 1 to 115.

Embodiment 126 is the apparatus or system of any one of embodiments 116 to 125, wherein the apparatus or system is further configured to isolate cells or macromolecules from the second portion of the aliquot.

Embodiment 127 is the apparatus or system of any one of embodiments 116 to 126, wherein the apparatus or system is further configured to amplify or sequence at least one nucleic acid from the second portion of the aliquot.

Embodiment 128 is the apparatus or system of any one of embodiments 116 to 127, wherein the apparatus or system is further configured to output a sample of wash liquid containing the first portion of the aliquot.

Embodiment 129 is the apparatus or system of any one of embodiments 116 to 128, wherein the apparatus or system is configured to add a sample of wash liquid containing the first portion of the aliquot to a culture medium.

Embodiment 130 is the apparatus or system of any one of embodiments 128 to 129, wherein the apparatus or system is configured to output the sample of wash liquid containing the first portion by transferring the sample into an output vessel.

Embodiment 131 is the apparatus or system of embodiment 130, wherein the apparatus or system comprises a pipettor and is configured to transfer the sample into an output vessel using the pipettor.

Embodiment 132 is the apparatus or system of embodiment 130 or 131, wherein the output vessel comprises a culture medium.

Embodiment 133 is the apparatus or system of embodiment 130 or 131, wherein the apparatus or system is further configured to transfer culture medium into the output vessel before, simultaneously with, or after transferring the sample of wash liquid containing the first portion into the output vessel.

Embodiment 134 is the apparatus or system of any one of embodiments 116 to 133, wherein the apparatus or system comprises a processor and a memory comprising instructions to perform the method of any one of embodiments 1 to 115.

Embodiment 135 is the use of a swab for processing a biological sample by associating the swab with an aliquot of a biological sample, transferring the swab into a wash liquid to release a first portion of the aliquot is released into the wash liquid, and transferring the swab into a carrier liquid, wherein a second portion of the aliquot is released into the carrier liquid.

Embodiment 136 is the use of embodiment 135, wherein the swab is held in a gripper during at least part of the use.

Embodiment 137 is the use of embodiment 136, wherein the gripper is a component of an apparatus or system for performing the method of any one of embodiments 1 to 115.

Embodiment 138 is the use of embodiment 136 or 137, wherein the gripper is a component of an apparatus or system configured to perform the method of any one of embodiments 1 to 115.

Embodiment 139 is the use of any one of embodiments 136 to 138, wherein the gripper is a component of an apparatus or system according to any one of embodiments 116 to 134.

DETAILED DESCRIPTION

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "an oligomer" includes a plurality of oligomers and the like. The conjunction "or" is to be interpreted in the inclusive sense, i.e., as equivalent to "and/or", unless the inclusive sense would be unreasonable in the context. Measured and measureable values are understood to be approximate, taking into account significant digits and the error associated with the measurement.

The use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components.

A. Overview

Certain types of biological samples, such as those containing particulate matter or viscous polymers, can be difficult to manipulate using pipets. Nonetheless, it is often desirable to process such samples prior to downstream analytical steps, e.g., by isolating cells or nucleic acids from other sample components, including where applicable the particulate matter or viscous polymers. As described in detail below, it has been found that a swab can be used to transfer an aliquot of a sample into a wash liquid to release a first portion of the aliquot into the wash liquid, followed by transferring the swab into a carrier liquid, wherein a second portion of the aliquot is released into the carrier liquid. The first portion can contain relatively more undesired material (e.g., particulate matter or viscous polymers) and the second portion can contain relatively more analyte (e.g., cells or nucleic acids). Thus, the presently disclosed methods can avoid the use of pipets and the attendant difficulties they present with certain types of samples while still achieving isolation of the analyte from the sample. The degree of isolation, while not necessarily absolute, can nonetheless be sufficient for downstream analytical steps such as nucleic acid amplification or other forms of detection or measurement.

B. Definitions

"Biological sample" includes any specimen that may contain a target material (e.g., cell, virus, nucleic acid, polypeptide, or other biomolecule), such as any tissue or material derived from or containing a living or dead organism or that may contain target material derived therefrom, including, e.g., peripheral blood, plasma, serum, lymph node, gastrointestinal tissue, cerebrospinal fluid, sputum, stool, urine, semen, vaginal secretion, saliva, biopsy material, other body fluids or materials, soil, sludge, or microbial growth such as a bacterial, archaeal, fungal, or protist colony or biofilm. The biological sample may be treated to physically or mechanically disrupt tissue or cell structure, thus releasing intracellular components into a solution or suspension, and/or combined with a buffer or other components. Also, biological samples include crude samples as discussed below and processed samples, such as those obtained from passing samples over or through a filtering device, or following centrifugation, or by adherence to a medium, matrix, or support.

A "crude sample" is a biological sample obtained directly from a living or dead organism, food, the environment, or the like, in contrast to extracts, lysates, filtrates, or eluates. Merely dissolving, suspending, or otherwise mixing crude material in or with a liquid does not convert it to a processed sample.

A "swab" is any device comprising a graspable region and absorbent or adsorbent material capable of associating with a biological sample in an at least partially reversible manner. Exemplary swabs include a rigid or semirigid rod as the graspable region with the absorbent or adsorbent material stably associated (e.g., adhered or bonded) at or near at least one end. The graspable region may be graspable by a human and/or a machine (e.g., robot).

A "wash liquid" is any liquid suitable for at least partially releasing undesired material (e.g., particulate matter and/or viscous polymers) in an aliquot of a biological sample from a swab. Where present, desired material such as cells (e.g., microbes) may also be released to some extent into a wash liquid.

A "carrier liquid" is any liquid suitable for at least partially releasing desired material (e.g., cells, viruses, or target nucleic acids or polypeptides) in an aliquot of a biological sample from a swab. Carrier liquids may also but do not necessarily contain additional substances for further processing a portion of the aliquot, e.g., by lysing cells or denaturing, inactivating, or degrading cellular components unwanted for a particular application and/or stabilizing, fixing, or preserving the sample or certain sample components such as cells, viruses, or target nucleic acids or polypeptides.

"Desired material" is typically released into a carrier liquid and contains analyte of interest, e.g., cells or macromolecules such as nucleic acids or polypeptides. In some cases desired material is also released into a wash liquid, and the identity of the desired material released into the wash liquid can differ from that released into the carrier liquid. For example, in some cases cells are the desired material released into the wash liquid and macromolecules such as nucleic acids or polypeptides are the desired material released into the carrier liquid. In other cases, the desired material released into both the wash liquid and the carrier liquid is the same (e.g., cells); in such cases the desired material can be processed differently, e.g., by preparing the cells in the wash liquid for culture, microscopy, or cytometry, and/or by lysing the cells in the carrier liquid for a subsequent molecular analysis.

"Undesired material" is typically released into a wash liquid and refers to material that is irrelevant to or may interfere with the intended use of desired material released into the carrier liquid. Examples of undesired material include viscous polymers such as polysaccharides and particulate matter. As a further example, where the desired material is nucleic acids, then undesired material can include lipids, glycoproteins, small molecules, and other impurities depending on the composition of the sample.

"Releasing" from an object into a liquid (e.g., from a swab into a wash or carrier liquid) means reducing the association of material so that that some (but not necessarily all) material carried into a liquid with the object remains in the liquid when the object is removed.

A liquid is "aqueous" if it is water, a mixture of water and a liquid miscible with water where the water is present in more than a trace amount, or a solution in which the solvent is any of the foregoing. In some embodiments, an aqueous liquid is at least 50% water by weight.

"Particulate matter" includes any material, excluding whole cells and cellular debris, of sufficient solidity to partially or completely obstruct the aperture of a pipet or micropipette tip. A solute dissolved in a solution is not particulate.

A "suspension" is a liquid containing undissolved solid or particulate matter.

"Aliquot" is used simply to denote some or all of a sample. First and second portions of an aliquot may or may not represent the entire aliquot.

Materials are "associated" if force (e.g., mechanical, gravitational, centrifugal, magnetic, or electrical) can be applied directly to one of the materials, such as a swab, in a way that moves it and the potentially associated material, such as a sample aliquot, in a common direction or to a common place (e.g., into a liquid, out of a liquid, or from a first liquid to a second liquid).

A "viscous polymer" is a polymer that is dissolved in sufficient quantity to detectably increase the viscosity of a liquid upon dissolution. In aqueous or polar liquids, viscous polymers can comprise a plurality of hydrogen bond donors and acceptors, such as hydroxyls, amines, oxos (carbonyl oxygens), etc., such that polymer molecules increase viscosity by exerting sufficient intermolecular attractive forces on a plurality of other polymer molecules and solvent molecules. Polysaccharides, polypeptides, nucleic acids, and various synthetic polymers can all be viscous polymers. Any suitable approach for measuring viscosity may be used. Exemplary instruments for determining viscosity include a capillary viscometer, Zahn cup, vibrational viscometer, and rotational viscometer.

A "polysaccharide" includes any linear or branched chain of sugars (including but not limited to amino sugars and sugar alcohols as well as true carbohydrates), which may or may not be conjugated (e.g., to a lipid or polypeptide) or derivatized (e.g., phosphorylated, acetylated, alkylated, or the like). Polysaccharide chains may use glycosidic or other bonds (e.g., phosphodiesters in certain polysaccharides such as poly-N-acetylmannosamine phosphate).

"Lipids" include fatty acids, triglycerides, phospholipids, sterols, steroids, waxes, and oils.

"Food" includes any material intended or suitable for consumption, including solids, suspensions, emulsions, and gels (thus including gelatin, milk, ice cream, fruit smoothies, emulsified cheese dips, fruit puree, nut butter, processed and/or textured protein, and the like as well as bread, fruit, vegetables, meat, etc., but not including clear, monodisperse solutions or water).

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, and combinations and analogs thereof such as "peptide nucleic acids" or PNAs (see, e.g., WO 95/32305) and "locked nucleic acids" (LNA), in which one or more nucleotide monomers have a bicyclic furanose unit locked in an RNA mimicking sugar conformation (see, e.g., Vester et al., Biochemistry 43:13233-41, 2004). A nucleic acid "backbone" may be made up of a variety of linkages, including one or more of sugar-phosphodiester linkages, peptide-nucleic acid bonds as in PNA, phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., The Biochemistry of the Nucleic Acids 5-36, Adams et al., ed., 11th ed., 1992; Abraham et al., 2007, BioTechniques 43: 617-24), which include derivatives of purine or pyrimidine bases (e.g., $N^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, etc., (see generally U.S. Pat. Nos. 5,378,825, 6,949,367 and International Patent Application Pub. No. WO 93/13121, each incorporated by reference herein), and/or "abasic" residues (see. e.g., U.S. Pat. No. 5,585,481, incorporated by reference herein). The term "polynucleotide" as used herein denotes a nucleic acid chain. A "nucleotide" is a subunit of a nucleic acid having a phosphate group, a 5-carbon sugar, and a nitrogenous base. The term also includes analogs of such subunits, such as a methoxy group at the 2' position of the ribose (also referred to herein as "2'-O-Me" or "2'-methoxy").

A "target" material (such as a target nucleic acid; other embodiments of target materials include cells, viruses, polypeptides, and other biomolecules) as used herein is a material to be detected or quantified. Target nucleic acids may be DNA or RNA as described herein, and may be either single-stranded or double-stranded. The target nucleic acid may include other sequences besides the target sequence, which may not be detected or quantified.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. An oligonucleotide may serve one or more of various different functions, e.g., as a primer and/or promoter, detection probe, capture oligomer, etc.

"Amplifying" or "amplification" refers to any known procedure for obtaining multiple copies of a target nucleic acid sequence or its complement or fragments thereof. The multiple copies may be referred to as amplicons or amplification products, which can be double-stranded or single-stranded and can include DNA, RNA, or both. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), helicase-dependent amplification, and transcription-mediated or transcription-associated amplification. Replicase-mediated amplification uses self-replicating RNA molecules, and a replicase such as QB-replicase (see. e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see. e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see. e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein). Helicase-dependent amplification uses a helicase to separate the two strands of a DNA duplex generating single-stranded templates, followed by hybridization of sequence-specific primers hybridize to the templates and extension by DNA polymerase to amplify the target sequence (see, e.g., U.S. Pat. No. 7,282,328, incorporated by reference herein). Amplification may be linear or exponential.

"Detection probe," "detection oligonucleotide," "probe oligomer," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Examples include invasive probes and primary probes, discussed below. Detection probes may be DNA, RNA, analogs thereof or combinations thereof (e.g., DNA/RNA chimerics) and they may be labeled or unlabeled. A detection probe's "target sequence" generally refers to a smaller nucleic acid sequence region within a larger nucleic acid sequence that hybridizes specifically to at least a portion of a probe oligomer by base pairing. A detection probe may comprise target-specific sequences and other sequences that contribute to the three-dimensional conformation of the probe (see. e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "probe system" is meant a plurality of detection oligomers or probes for detecting a target sequence. In some embodiments, a probe system comprises at least primary and secondary probes, at least invasive and primary probes, or invasive, primary, and secondary probes. An "invasive probe" refers to an oligonucleotide that hybridizes to a target nucleic acid at a location near the region of hybridization between a primary probe and the target nucleic acid, wherein the invasive probe oligonucleotide comprises a portion (e.g., a chemical moiety, or nucleotide, whether complementary to that target or not) that overlaps with the region of hybridization between the primary probe oligonucleotide and the target nucleic acid. The "primary probe" for an invasive cleavage assay includes a target-specific region that hybridizes to the target nucleic acid, and further includes a "5' flap" region that is not complementary to the target nucleic acid. In some embodiments, a primary probe comprises a target-hybridizing sequence and a non-target-complementary sequence. In some embodiments, a primary probe undergoes nucleolysis (e.g., cleavage, such as 5'-cleavage or endonucleolysis) upon hybridization to a target sequence in the presence of an appropriate nuclease, such as structure-specific nuclease, e.g., a cleavase or 5'-nuclease. In some embodiments, such nucleolysis results in liberation of a "flap" or cleavage fragment from the primary probe that interacts with the secondary probe. In some embodiments, the secondary probe comprises at least one label. In some embodiments, the secondary probe comprises at least a pair of labels, such as an interacting pair of labels, e.g., a FRET pair or a fluorophore and quencher. In some embodiments, interaction of the secondary probe with a liberated flap of the primary probe results in a detectable change in the emission properties of the second probe, e.g., as discussed below with respect to INVADER® assays, FRET, and/or quenching. In some embodiments, a probe system comprises a primary probe and a secondary probe configured to interact with a liberated flap of the primary probe, e.g., the primary probe can be cleaved to give a liberated flap sufficiently complementary to the secondary probe or a segment thereof to form a complex.

As used herein, the term "invasive cleavage structure" (or simply "cleavage structure") refers to a structure comprising: (1) a target nucleic acid, (2) an upstream nucleic acid (e.g., an invasive probe oligonucleotide), and (3) a downstream nucleic acid (e.g., a primary probe oligonucleotide), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, as disclosed, for example, in U.S. Pat. No. 6,090,543. In some embodiments, one or more of the nucleic acids may be attached to each other, for example through a covalent linkage such as nucleic acid stem-loop, or through a non-nucleic acid chemical linkage (e.g., a multi-carbon chain). An invasive cleavage structure also is created when a cleaved 5' flap hybridizes to a FRET cassette (i.e., when the "target nucleic acid" and the "downstream nucleic acid" are covalently linked in a stem-loop configuration). The "target nucleic acid" sequence of a FRET cassette that hybridizes to a cleaved 5' flap can be referred to as a "5' flap-hybridizing sequence."

As used herein, an "INVADER® assay" or "invasive cleavage assay" refers to an assay for detecting target nucleic acid sequences in which an invasive cleavage structure is formed and cleaved in the presence of the target sequence. In some embodiments, reagents for an invasive cleavage assay include: a cleavage agent; and oligonucleotides (e.g., an "invasive probe," a "primary probe," and a "FRET cassette"). In some embodiments, the invasive probe is an amplification oligomer or extension product thereof. The invasive cleavage assay can combine two invasive signal amplification reactions (i.e., a "primary reaction" and a "secondary reaction") in series in a single reaction mixture. In some embodiments, detecting the presence of an invasive cleavage structure is achieved using a cleavage agent. The primary probe can be part of a probe system. In some embodiments, an additional portion of the primary probe comprises or consists of a 3' terminal nucleotide which is not complementary to the target nucleic acid and/or which is non-extendable. In some embodiments, an additional portion of the primary probe is configured to interact with a FRET cassette, e.g., comprises a FRET cassette interacting-sequence, e.g., which is not complementary to the target nucleic acid. In some embodiments, the reagents for an INVADER® assay further comprise a nuclease, e.g., a cleavase, e.g., a FEN enzyme (e.g., Afu, Ave, RAD2 or XPG proteins) or other enzyme (e.g., a DNA polymerase with 5' nuclease activity, optionally with inactivated or reduced synthetic activity) wherein the nuclease has activity specific for a structure formed when both the invasive and primary probes are hybridized to a target sequence (e.g., a structure that can result when a duplex of the primary probe and the target undergoes 3'-end invasion by the invasive probe, wherein at least the 3' end and/or an intermediate portion of the invasive probe is hybridized, the 5' end of the primary probe is free, and an intermediate and/or 3'-terminal portion of the primary probe is hybridized). In some embodiments, the reagents for an INVADER® assay further comprise a buffer solution. In some embodiments, the buffer solution comprises a source of divalent cations (e.g., $Mn^{2+}$ and/or $Mg^{2+}$ ions, such as a magnesium salt or manganese salt, e.g., $MgCl_2$, $MnCl_2$, magnesium acetate, manganese acetate, etc.). In some embodiments, the reagents for an INVADER® assay further comprise at least one third oligomer, such as at least one amplification oligomer that together with the first oligomer is configured to produce an amplicon, e.g., via PCR. In such embodiments, the primary probe can comprise a target-hybridizing sequence configured to specifically hybridize to the amplicon. In some embodiments, the reagents for an INVADER® assay further comprise amplification reagents, such as PCR reagents. Embodiments of an INVADER® assay in which the target sequence is amplified can be referred to as INVADER PLUS® assays. Including amplification in the assay can provide a beneficially low limit of detection. INVADER® assays, cleavases, other nucleases, other possible INVADER®/INVADER PLUS® reagents, etc., are discussed, for example, in U.S. Pat. Nos. 5,846,717, 5,985,557, 5,994,069, 6,001,567, 6,913,881, 6,090,543, 7,482,127, and 9,096,893; WO 97/27214; WO 98/42873; Lyamichev et al., Nat. Biotech., 17:292 (1999); Hall et al., PNAS, USA, 97:8272 (2000); and WO 2016/179093, which are each incorporated by reference herein.

As used herein, the term "flap endonuclease" or "FEN" (e.g., "FEN enzyme") refers to a class of nucleolytic enzymes that act as structure-specific endonucleases on DNA structures with a duplex containing a single-stranded 5' overhang, or flap, on one of the strands that is displaced by another strand of nucleic acid, such that there are overlapping nucleotides at the junction between the single and double-stranded DNA. FEN enzymes catalyze hydrolytic cleavage of the phosphodiester bond 3' adjacent to the junction of single and double stranded DNA, releasing the overhang, or "flap" (see Trends Biochem. Sci. 23:331-336 (1998) and Anna. Rev. Biochem. 73: 589-615 (2004)). FEN enzymes may be individual enzymes, multi-subunit enzymes, or may exist as an activity of another enzyme or protein complex, such as a DNA polymerase. A flap endonuclease may be thermostable. Examples of FEN enzymes useful in the methods disclosed herein are described in U.S. Pat. Nos. 5,614,402; 5,795,763; 6,090,606; and in published PCT applications identified by WO 98/23774; WO 02/070755; WO 01/90337; and WO 03/073067, each of which is incorporated by reference in its entirety. Particular examples of commercially available FEN enzymes include the Cleavase® enzymes (Hologic, Inc.).

"Cassette," when used in reference to an INVADER assay and/or invasive cleavage assay or reaction, as used herein refers to an oligomer or combination of oligomers configured to generate a detectable signal in response to cleavage of a detection oligomer in an INVADER assay. In some embodiments, the cassette hybridizes to a cleavage product (e.g., a "flap") from cleavage of the detection oligomer (e.g., primary probe). In some embodiments, such hybridization results in a detectable change in fluorescence. In some embodiments, such hybridization forms a second invasive cleavage structure, such that the cassette can then be cleaved. In some embodiments, a cassette comprises an interacting pair of labels, e.g., a FRET pair (in which case the cassette is a "FRET cassette"). In some embodiments, a FRET cassette undergoes a detectable change in fluorescence properties upon hybridization to a cleavage product from cleavage of the detection oligomer. For example, a FRET cassette can increase fluorescence emission at a first wavelength and/or decrease fluorescence emission at a second wavelength based on a change in the average distance between labels upon hybridization to a cleavage product from cleavage of the detection oligomer. This can result from a decrease in energy transfer from a donor fluorophore (e.g., a decrease in quenching of a fluorophore or a decrease in energy transfer from a donor fluorophore to an acceptor fluorophore). In some embodiments, a FRET cassette adopts a hairpin conformation, wherein the interaction of the pair of labels substantially suppresses (e.g., quenches) a detectable energy emission (e.g., a fluorescent emission). In some embodiments, a FRET cassette comprises a portion that hybridizes to a complementary cleaved 5' flap of a primary probe to form an invasive cleavage structure that is a substrate for a cleavage agent (e.g., FEN enzyme). In some embodiments, cleavage of the FRET cassette by a cleavage agent separates the donor and acceptor moieties with the result of relieving the suppression and permitting generation of a signal.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties.

"Capture probe," "capture oligonucleotide," "capture oligomer," "target capture oligomer," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly-U sequences to bind non-specifically to a target nucleic acid and link it to an immobilized probe on a support.

"Separating" or "purifying" means that one or more components of a sample are removed or separated from other sample components. Sample components include target material, e.g., target nucleic acids, are usually in an aqueous solution phase, which may also include suspended material, cellular fragments, proteins, carbohydrates, lipids, and other nucleic acids. "Separating" or "purifying" does not connote any particular degree of purification. In some embodiments, separating or purifying reduces the amount or concentration of other sample components by at least 70%, or at least 80%, or at least 95%. In some embodiments, separating or purifying renders the target material at least 70%, or at least 80%, or at least 95% pure.

C. Exemplary Methods

1. Contacting a Biological Sample with a Swab, Wherein an Aliquot of the Biological Sample and the Swab Become Associated; Swabs; Samples Methods disclosed herein use a swab associated with an aliquot of a biological sample. In some embodiments, methods according to the disclosure can comprise contacting the biological sample with the swab, wherein an aliquot of the biological sample and the swab become associated. The association between the sample aliquot and the swab should be temporary or reversible at least in part, so that at least some undesired material (e.g., particulate matter or viscous material) can be released in a wash liquid and at least some analyte (e.g., cells or nucleic acid) can be released subsequently in a carrier liquid. One skilled in the art can choose an appropriate manner of contacting the sample with the swab so as to achieve a suitable association of the sample aliquot with the swab, e.g., dipping, wiping, poking, or spinning the swab into, on, or across the sample.

Any swab suitable for adsorbing and releasing biological material can be used. In some embodiments, a swab is used that comprises a stem with absorbent and/or adsorbent material (e.g., sponge or fibers, which can be, e.g., cotton, alginate, silk, carbon fiber, or polymeric fibers, such as rayon, polyester, or polyamide) wrapped around, bonded, or adhered to an end to form a tip, the absorbent or adsorbent material being suitable for adsorbing and/or absorbing the sample to be collected. In some embodiments, the tip has a thickness (measured perpendicularly to the stem axis) of 0.5 to 3 mm. In some embodiments, the tip comprises fibers having a linear density of 1 to 4 mg per 10 meters.

In some embodiments, a flocked swab is used comprising an elongate support body and a plurality of flocked fibers at an end of the support. Exemplary flocked swabs are described in US 2006/0142668, which is incorporated herein by reference. Swabs can have elongate stems generally made of plastic materials, for example polystyrene.

In some embodiments, a swab further comprises a surfactant, which may assist in liberating sample material, e.g., associated with a solid substrate or surface so that it is available to become associated with the swab. In some embodiments, the surfactant is cationic, e.g., comprises a quaternary amine, such as benzalkonium. In some embodiments, the surfactant comprises chloride, e.g., a quaternary amine chloride, such as benzalkonium chloride. See US 2012/0171712 (incorporated herein by reference) for further discussion of swabs and surfactants.

Any biological sample that can become associated with a swab can be used in methods according to the disclosure. Biological samples used in methods according to the disclosure can be emulsions, suspensions, or solutions (or a combination thereof) and can comprise various types of impurities or contaminants, such as viscous polymers or particulate matter. Particulate matter can include incompletely digested or indigestible material derived from food, solid lipids, inorganic solids such as phosphates (e.g., calcium or iron phosphate), and insoluble fibrous matter (e.g., cellulose fibers). Viscous polymers can include polysaccharides (e.g., mucopolysaccharides, lipopolysaccharides, proteoglycans, starch, glycogen, or soluble cellulose), extracellular nucleic acids, and polypeptides (including glycoproteins and lipopolypeptides). A sample can comprise a lipid phase or a lipid emulsion. A sample can comprise cellular debris, which depending on its size, solubility, and hydrophobicity may occur at least in part as particulate matter, viscous polymers, a lipid phase or emulsion, or a combination thereof. Samples can be crude or may have undergone some initial purification, such as filtration, extraction, or fractionation (e.g., chromatographic). In some embodiments, a crude sample is diluted, suspended, or at least partially dissolved with a suitable liquid such as water or a solution, which may be buffered, saline, or isotonic with the sample.

In some embodiments, the biological sample is a stool sample. Stool samples can comprise particulate matter such as incompletely digested or indigestible material derived from food, solid lipids, inorganic solids such as phosphates (e.g., calcium or iron phosphate), and insoluble fibrous matter (e.g., cellulose fibers). Stool samples can also comprise viscous polymers including polypeptides, polysaccharides, and extracellular nucleic acids as discussed above. Stool samples can also comprise a lipid phase or a lipid emulsion. Stool samples also generally comprise bacteria, which depending on the application may include normal gut flora or enteropathogens (e.g., *C. difficile*) or a combination thereof.

Other exemplary sample types that may include particulate matter, viscous polymers, or emulsions are sputum, mucus such as nasal mucus, blood, soil, sludge, or a microbial growth. Sludge and soil include natural and artificial versions thereof, such as mud, potting mix, chemical waste, etc. Microbial growths include bacterial, archaeal, protist, or fungal growths, such as colonies, biofilms, mycelia, etc. In some embodiments, the sample is a food sample.

In some embodiments, a sample comprises or is suspected of comprising a pathogen, virus, fungus, or bacterium. In some embodiments, the bacterium or fungus is a spore. Exemplary pathogens, viruses, and bacteria include *Clostridium* (e.g., *C. difficile, C. botulinum*), Staphylococci (e.g., *S. aureus*, such as MRSA), norovirus, *E. coli* (e.g., enteroaggregative, enterotoxinogenic, enteropathogenic, or enteroinvasive strains, or *E. coli* O157), *Shigella* (e.g., *S. flexneri, S. dysenteriae, S. boydii, S. sonnei, S. paratyphi*), *Bacillus* (e.g., *B. cereus*), Rotavirus (e.g., Rotavirus A), Norwalk agent, *Vibrio* (e.g., *V. cholerae, V. vulnificus, V. parahemolyticus*), *Salmonella* (e.g., *S. typhimurium, S. typhi, S. enteriditis*), *Campylobacter* (e.g., *C. jejuni, C. coli, C. upsaliensis*), *Plesiomonas* (e.g., *P. shigelloides*), *Yersinia* (e.g., *Y. pestis*), *Cryptosporidium* (e.g., *C. parvum*), *Cyclospora* (e.g., *C. cayetanensis*), *Entamoeba* (e.g., *E. histolytica*), Adenovirus (e.g., serotype 40 or 41), or a Sapovirus (e.g., Sapporo virus).

Any volume of material sufficient to give an adequate second portion for the intended downstream use, as the case may be, can be associated with the swab. In some embodiments, a volume of 20 to 350 microliters of sample, such as 20 to 50, 50 to 100, 100 to 150, 150 to 200, 200 to 250, 250 to 300, or 300 to 350 microliters or 20 to 75, 75 to 125, 125 to 175, 175 to 225, 225 to 275, or 275 to 350 microliters becomes associated with the swab.

2. Transferring the Swab into a Wash Liquid, Wherein a First Portion of the Aliquot is Released into the Wash Liquid; Wash Liquids Methods according to the disclosure can comprise transferring the swab into a wash liquid, wherein a first portion of the aliquot is released into the wash liquid. The release of the first portion into the wash liquid can be achieved in any suitable manner, and can comprise one or more forms of agitation such as spinning, shaking, swirling, stirring, vortexing, etc. In some embodiments, the agitation occurs for a period of 0.5 to 15 seconds, e.g., 0.5 to 2 seconds, 2 to 4 seconds, 4 to 6 seconds, 6 to 8 seconds, 8 to 10 seconds, 10 to 12 seconds, or 12 to 15 seconds, although longer or shorter periods may be desirable depending on the circumstances such as how tightly the aliquot is associated with the swab. Depending on the nature of the sample, certain approaches may be particularly suitable for releasing the first portion. For example, samples that already contain surfactant and/or may be more amenable to release by swirling or spinning, while denser or more adhesive samples may benefit from more vigorous agitation such as vortexing or shaking. When a wash liquid containing a detergent is used, it may be desirable to use a type of agitation that minimizes foaming, such as spinning, swirling, or stirring at low enough speeds to mostly avoid bubble formation.

In some embodiments, the swab is pressed against the wall of a vessel containing the wash liquid during at least some of the time it is in the wash liquid, such as during at least some of the time that the swab is being agitated in the wash liquid. Alternatively, it is possible in some situations that a portion of the aliquot may be sufficiently loosely associated and/or a wash liquid is used such that merely placing the swab in the wash liquid will release the first portion into the wash liquid, either at or just after the time when the swab is transferred into the wash liquid or after remaining in the liquid for some time, e.g., 1-5 seconds, 5-10 seconds, 10-20 seconds, 20-30 seconds, 30-60 seconds, 1-2 minutes, 2-3 minutes, 3-5 minutes, or 5-10 minutes. For example, wash liquids containing one or more of an organic cosolvent, detergent, or salt may facilitate release of the first portion at or after the time when the swab is transferred into the wash liquid, although such liquids can also be used with agitation as discussed above.

The wash liquid can be water or an aqueous solution. In some embodiments, the aqueous solution comprises a salt, e.g., NaCl or KCl. In some embodiments, the aqueous solution comprises a buffer, e.g., Tris, MOPS, or phosphate buffer. In some embodiments, the aqueous solution comprises a detergent, e.g., an alkyl sulfate detergent or a glycoside detergent. In some embodiments, the aqueous solution comprises an organic cosolvent, such as an alcohol, e.g., methanol, ethanol, or isopropanol. To be clear, a liquid (including both wash liquids and carrier liquids discussed below) is considered an aqueous solution even if an organic cosolvent is present in a greater amount (by weight, volume, or mole fraction) than water. Depending on the nature of the sample, certain wash liquid components may be particularly appropriate. For example, release of hydrophobic material can be facilitated by organic cosolvents and/or detergents, while release of some viscous polymers such as polypeptides, polysaccharides, and combinations thereof may be facilitated by substances that stabilize the polymers in a dispersed state, e.g., buffers, salts, detergents, etc.

In some embodiments, the wash liquid is used in a further analytical step after release of the first portion of the aliquot. For example, where the sample comprises or is suspected of comprising microbes, a culturing step can be performed using the wash liquid containing the first portion of the aliquot or a sample thereof. Thus, in some embodiments, the wash liquid is a culture medium, or contains components compatible with a culture medium. As a further example, where the sample comprises or is suspected of comprising cells, the wash liquid containing the first portion of the aliquot or a sample thereof can be subjected to an optical analytical procedure such as flow cytometry or microscopy.

3. Transferring the Swab into a Carrier Liquid, Wherein a Second Portion of the Aliquot is Released into the Carrier Liquid; Carrier Liquids Methods according to the disclosure can comprise transferring the swab into a carrier liquid, wherein a second portion of the aliquot is released into the carrier liquid. The carrier liquid can be water or an aqueous solution. In some embodiments, the aqueous solution comprises a salt, e.g., NaCl or KCl. In some embodiments, the aqueous solution comprises a buffer, e.g., Tris, MOPS, or phosphate buffer. In some embodiments, the aqueous solution comprises an organic cosolvent, such as an alcohol, e.g., methanol, ethanol, or isopropanol. In some embodiments, the aqueous solution comprises a detergent, e.g., an alkyl sulfate detergent or a glycoside detergent. In some embodiments, the aqueous solution comprises an organic cosolvent. In some embodiments, the aqueous solution comprises a base, e.g., a hydroxide, such as an alkali hydroxide, such as NaOH, KOH, or LiOH. In some embodiments, the carrier liquid is a lysis solution. Various lysis solutions are known in the art and may comprise one or more of a base and a detergent, and may further comprise a salt, examples of all of which are given above. In some embodiments, the carrier liquid further comprises one or more preservatives, such as one or more preservatives that inhibit nucleic acid degradation, e.g., one or more of an RNase inhibitor or divalent ion chelator (e.g., EGTA or EDTA).

Carrier liquid components can be selected so as to facilitate release of the second portion and/or stabilize, fix, or preserve analyte contained therein. For example, salt may facilitate the release of proteinaceous material and stabilize it in a disperse state, as may detergents, with nonionic detergents being more likely to allow the material to retain a more native conformation and ionic detergents more likely to denature the protein; either may be desirable depending on the particular application. Organic cosolvents can facilitate release of hydrophobic material and can also contribute to preservation or fixation of cells. RNase inhibitors or divalent ion chelators can inhibit analyte degradation.

The release of the second portion of the aliquot into the carrier liquid can be achieved in any suitable manner, and can comprise one or more forms of agitation such as spinning, shaking, swirling, stirring, vortexing, etc. In some embodiments, the agitation occurs for a period of 0.5 to 15 seconds, e.g., 0.5 to 2 seconds, 2 to 4 seconds, 4 to 6 seconds, 6 to 8 seconds, 8 to 10 seconds, 10 to 12 seconds, or 12 to 15 seconds, although longer or shorter periods may be desirable depending on the circumstances such as how tightly the remaining aliquot is associated with the swab. Where the sample material is visible (e.g., due to presence of chromophores or material that increases turbidity such as cells), it may be readily apparent when release has occurred based on changes in the visual properties of the wash liquid such as color and turbidity. Alternatively, if desired, or to determine an appropriate protocol in a particular application, release of the second portion can be confirmed or determined using analytical procedures for quantification of cells, nucleic acids, polypeptides, and the like known in the art such as spectrophotometry, microscopy, ELISA, etc.

In some embodiments, the swab is pressed against the wall of a vessel containing the carrier liquid during at least some of the time it is in the carrier liquid, such as during at least some of the time that the swab is being agitated in the carrier liquid. Alternatively, it is possible in some situations that a portion of the aliquot may be sufficiently loosely associated so that merely placing the swab in the carrier liquid will release the second portion into the carrier liquid, either at or just after the time when the swab is transferred into the carrier liquid or after remaining in the liquid for some time, e.g., 1-5 seconds, 5-10 seconds, 10-20 seconds, 20-30 seconds, 30-60 seconds, 1-2 minutes, 2-3 minutes, 3-5 minutes, or 5-10 minutes.

In some embodiments, cells are released from the swab into the carrier liquid. In some embodiments, nucleic acid is released from the swab into the carrier liquid. The cells or nucleic acid can be further processed and/or characterized in any number of ways.

4. Further Processing and/or Analysis of Sample Material Including Cells, Nucleic Acids, or Polypeptides; Capture, Amplification, and Detection of Targets; Target Bacterial or Pathogen Sequences In some embodiments, cells released into the carrier liquid are lysed, e.g., by heating, sonication, osmolysis, exposure to alkali and/or detergent, or a combination thereof. This can occur in the carrier liquid, either commencing immediately upon transferring the swab into the carrier liquid such as in the case of the carrier liquid being a lysis solution, or afterward, e.g., as in the case of further manipulation by addition of reagents or use of equipment following release of the second portion of the aliquot into the carrier liquid. In some embodiments, nucleic acids are isolated from the lysate, e.g., by chromatography or precipitation, or binding to a binding agent, such as at least one capture oligomer. In some embodiments, polypeptides are isolated from the lysate, e.g., by chromatography, precipitation, or binding to an affinity binding partner such as an aptamer, or antibody, or other affinity binding partner.

In some embodiments, nucleic acids released from the swab into the carrier liquid or from cells released and lysed as discussed above are further isolated or purified. For example, further isolation or purification can be performed using chromatography or precipitation, or by binding nucleic acid to a binding agent, such as at least one capture oligomer. For example, it can be beneficial to further isolate or purify nucleic acids intended to be subjected to downstream analytical approaches, e.g., amplification or sequencing, that may otherwise be inhibited in whole or part due to impurities.

Where at least one capture oligomer is used, it can be sequence-specific (i.e., it comprises a target-hybridizing region configured to specifically hybridize to a site in the target nucleic acid to form a duplex). One example of a capture oligomer includes two binding regions: a sequence-binding region (e.g., target-specific portion) and an immobilized probe-binding region, usually on the same oligomer, although the two regions may be present on two different oligomers joined together by one or more linkers. Alternatively, capture oligomers with randomized, repeating, or non-specific sequences for hybridization to a target can be used, such as poly-(k) and poly-(r) capture oligomers and combinations thereof, which are described, e.g., in US 2013/0209992 and in U.S. Provisional Application No. 62/504,900 filed May 11, 2017, which are incorporated herein by reference. In some embodiments, a capture oligomer uses a target-sequence binding region that includes random or non-random poly-GU, poly-GT, or poly-U sequences to bind non-specifically to a target nucleic acid. In some embodiments, a capture oligomer uses a target-sequence binding region that includes random or non-random poly-GA, sequences to bind non-specifically to a target nucleic acid. In some embodiments, a combination of capture oligomers is used in which a first capture oligomer comprises random or non-random poly-GA, sequences and the second capture oligomer comprises random or non-random poly-GU or poly-GT sequences. The capture oligomers can further comprise a sequence or moiety that binds an immobilized probe on a support.

In some embodiments, a method further comprises determining the presence or absence of at least one macromolecule in the sample. In some embodiments, nucleic acids isolated from the lysate can be subjected to one or more analytical procedures such as detection of the presence or absence of one or more target sequences (e.g., using one or more probes, such as probe oligomers, for the target regions, which can follow amplification of the target sequences or can be performed on isolated nucleic acid directly, as in Southern, slot, or dot blotting); sequencing; electrophoresis; molecular cloning; or microarray analysis. In some embodiments, an amplification reaction is performed such as PCR, TMA, or any other type of amplification including those discussed above.

In some embodiments, a probe oligomer or FRET cassette is used that comprises a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see. e.g., U.S. Pat. Nos. 6,180,340 and 6,350,579, each incorporated by reference herein). Labels may be attached to a probe by various means including covalent linkages, chelation, and ionic interactions, but in some embodiments the label is covalently attached. For example, in some embodiments, a detection probe has an attached fluorescent or chemiluminescent label such as, e.g., an acridinium ester (AE) compound (see. e.g., U.S. Pat. Nos. 5,185,439; 5,639,604; 5,585,481; and 5,656,744; each incorporated by reference herein), which in typical variations is attached to the probe by a non-nucleotide linker (see. e.g., U.S. Pat. Nos. 5,585,481; 5,656,744; and 5,639,604, each incorporated by reference herein). In some embodiments, a probe oligomer is labeled with an interactive pair of detectable labels. Examples of detectable labels that are members of an interactive pair of labels include those that interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

In some embodiments, at least one probe system is used, wherein the oligomers of the system function together to facilitate detection of a target sequence. For example, in INVADER or INVADER PLUS assays, an invasive oligomer (which can also but does not necessarily function as an amplification oligomer, e.g., primer), a primary probe, and a FRET cassette can be used. INVADER and INVADER PLUS assays are discussed in detail above.

A detection probe oligomer in accordance with the present disclosure can comprise a non-target-hybridizing sequence. In some applications, probes exhibiting at least some degree of self-complementarity are desirable to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Particularly suitable hairpin probes include a "molecular torch" (see. e.g., U.S. Pat. Nos. 6,849,412; 6,835,542; 6,534,274; and 6,361,945, each incorporated by reference herein) and a "molecular beacon" (see. e.g., U.S. Pat. Nos. 5,118,801, 5,312,728, and 5,925,517, each incorporated by reference herein). In yet other embodiments, a detection probe is a linear oligomer that does not substantially form conformations held by intramolecular bonds.

In some embodiments, an amplification and detection procedure is performed such as an INVADER or INVADER PLUS assay, a TaqMan assay, or a TMA reaction with probe hybridization and detection (e.g., using at least one probe oligomer or FRET cassette comprising a fluorophore and a FRET partner and exhibiting hybridization-dependent and/or degradation-dependent fluorescence). In some embodiments, detection is in real time during the amplification reaction. In some embodiments, detection occurs near, at, or after the end of the amplification reaction. In some embodiments, at least one target sequence is quantified, e.g., based on a standard curve and/or one or more calibration standards.

Where the sample comprises or is suspected of comprising a pathogen, the method can comprise determining the presence or absence of at least one nucleic acid characteristic of the pathogen. For example, where the pathogen is *C. difficile*, the method can comprise determining the presence or absence of at least one of tcdB, tcdC, and cdtB, which are toxin-encoding or toxin-regulating genes found in various pathogenic *C. difficile* strains. See, e.g., Huang et al., *J. Clin. Microbiol.* 47:3729-3731 (2009), which is incorporated herein by reference. As a further example, where the pathogen is methicillin-resistant *Staphylococcus aureus* (MRSA), the method can comprise determining the presence or absence of at least one of an orfX/SCCmec junction, a mecA or mecC sequence, and an *S. aureus*-specific sequence. See, e.g., U.S. Provisional Application No. 62/544,491, filed Aug. 11, 2017; US 2013/0266942; US 2008/0227087; and US 2005/0019893, which are incorporated herein by reference.

In some embodiments, polypeptides isolated from the lysate can be subjected to one or more analytical procedures such as detection of the presence or absence of one or more target or other forms of characterization, which may include one or more of an antibody or aptamer-binding assay (e.g., ELISA or Western blot); electrophoresis; amino acid sequencing; or mass spectrometry. In some embodiments, at least one polypeptide is quantified, e.g., based on a standard curve and/or one or more calibration standards.

In some embodiments, cells released into the carrier liquid are fixed, e.g., with an aldehyde or other cross-linking agent. In some embodiments, the cells are stained, e.g., with a fluorescent dye or chromophore, which is optionally linked to a binding agent such as a nucleic acid probe (e.g., FISH probe), antibody, or aptamer. In some embodiments, the cells are subjected to flow cytometry, microscopy, or other optical analysis.

D. Apparatuses and Systems

Also provided are apparatuses and systems for processing biological samples, which can be configured to perform a method described herein. An apparatus is used to refer to a manufactured object comprising components that perform one or more functions, while a system can comprise more than one object operably linked (such as through electronic, mechanical, or optical/wireless communication) to collectively perform one or more functions. An exemplary type of system is one in which a computer is electronically or wirelessly linked to an apparatus comprising physical components for performing the method, such as grasping components, one or more receptacles, etc., so as to control the apparatus in performing a sample processing method. Another exemplary type of system is one in which a first apparatus and a second apparatus function cooperatively to perform the tasks for which they are configured; for example, a first apparatus can be configured to perform tasks involving manipulating a swab and outputting processed samples for subsequent steps, and a second apparatus can be configured to receive processed samples and perform subsequent steps, such as liquid handling and/or analytical procedures, including but not limited to addition of culture media and/or one or more molecular assays such as one or more nucleic acid amplification reactions.

In some embodiments, the system or apparatus comprises a gripper for holding a swab. The gripper can be a ring, gasket, clamp, grasper, or claw. For example, inflatable or compressible rings or gaskets can be used to grip the swab, wherein inflation or pressure is used to contract the interior diameter of the ring or gasket to provide a sufficiently firm grip to hold and optionally move and/or agitate the swab. The gripper can be used to transfer the swab into the wash liquid and from the wash liquid into the carrier liquid. In some embodiments, the gripper is associated with a motor to agitate the swab in at least one of the wash liquid or the carrier liquid (e.g., in any of the manners of agitation discussed above), or to move the swab, e.g., into the wash liquid and/or from the wash liquid into the carrier liquid. In some embodiments, the system or apparatus comprises a motor to agitate at least one of the wash liquid or the carrier liquid (e.g., in any of the manners of agitation discussed above), such as when the swab is present in such liquid, to facilitate release of material into the liquid. The gripper can obtain the swab from a container; the swab may be provided already associated with an aliquot of the sample, or the system or apparatus can be provided with the sample so that it can perform the contacting step to effect such association. The gripper can release the swab, e.g., into a waste container, after the second portion of the aliquot has been released. Grippers (e.g., for holding tubes) and related components such as motors are discussed in US2016/0077118, which is incorporated herein by reference for all purposes. The grippers of US2016/0077118 can be used or adapted for use with swabs by one skilled in the art.

In some embodiments, the apparatus or system comprises a processor and a memory comprising instructions to perform a method disclosed herein.

In some embodiments, the apparatus or system comprises a receptacle for holding at least one container, such as tubes, plates, cups, flasks, beakers, and the like for holding the sample, wash liquid and/or carrier liquid. An exemplary type of receptacle is a rack, although any type of receptacle that can hold the desired container(s) can be used. In some embodiments, the receptacle is associated with a motor, so that the container(s) can be brought to the swab in the course of performing sample processing.

In some embodiments, the apparatus or system comprises at least one reservoir for holding wash liquid or carrier liquid, or at least first and second reservoirs for holding wash liquid and carrier liquid, respectively. The apparatus or system can comprise tubing for transporting at least one of wash liquid and carrier liquid from the reservoir(s) into at least one container, which can then be used in the sample processing method.

In some embodiments, the apparatus or system is further configured to isolate analyte such as cells or macromolecules from the second portion of the aliquot. For example, the apparatus or system can be configured to precipitate, centrifuge, or capture (e.g., with capture probes) the analyte.

In some embodiments, the apparatus or system is further configured to amplify or sequence at least one nucleic acid from the second portion of the aliquot. Components, apparatuses, and systems for amplifying or sequencing nucleic acids are known in the art (see, e.g., U.S. Pat. No. 9,465,161; US 2012/0003646; and U.S. Pat. No. 8,315,817) and can be included in a system or apparatus according to the present disclosure.

In some embodiments, the apparatus or system is further configured to output a sample of wash liquid containing the first portion of the aliquot. For example, the output sample can be output into an output vessel, such as a vial, tube, capillary, or multiwell plate. The apparatus or system can comprise a pipettor or any other suitable equipment for outputting the output sample, e.g., transferring it into an output vessel. See, e.g., US2016/0077118, supra, for further discussion of pipettors and other liquid handling components. This can be useful in situations where the wash liquid containing the first portion of the aliquot is to be used in a subsequent analysis, such as culturing to determine or confirm the presence of a microorganism of interest (e.g., a pathogen, such as *C. difficile* or MRSA) or an optical analytical procedure such as flow cytometry or microscopy, e.g., to characterize cells present in the aliquot. In embodiments related to culturing, the wash liquid itself can be a culture medium, a culture medium can be added to the output sample, or the output sample can be added to or mixed with a culture medium.

EXAMPLES

The following are provided to illustrate certain disclosed embodiments and are not to be construed as limiting the scope of this disclosure in any way.

Methods for processing samples in preparation for nucleic acid detection were compared as follows.

Four independent human stool samples containing *C. difficile* were each processed in three ways: pipet transfer; primary swab transfer; or secondary swab transfer. The wash liquid was about 300 μl of culture medium (Liquid Amies transport medium). The carrier liquid was about 600 μl of a lysis buffer containing 400 mM LiOH and 10% (w/v) lithium lauryl sulfate. Three technical replicates were performed for each sample and each processing approach.

For pipet transfer, 100 μl of the stool sample was pipetted into the wash liquid, which was mixed, and then 100 μl of this mixture was pipetted into the carrier liquid.

For primary swab transfer, a flocked swab (Copan Diagnostics, Inc.) was dipped in the stool sample so as to fully wet it, adsorbing a volume of about 140 μl. The swab was then removed and dipped in the wash liquid and manually rotated clockwise and counterclockwise to release a portion of the sample. The swab was then removed and dipped in the carrier liquid and manually rotated clockwise and counterclockwise, followed by pressing the swab against the side of the vial containing the carrier liquid above the surface of the liquid to release additional material.

For secondary swab transfer, a flocked swab (Copan Diagnostics, Inc.) was dipped in the stool sample so as to fully wet it, adsorbing a volume of about 140 μl. The swab was then removed and dipped in the wash liquid and manually rotated clockwise and counterclockwise to release a portion of the sample. The swab was then removed. A second, fresh swab was then dipped in the mixture so as to fully wet it, adsorbing a volume of about 140 μl. The second swab was then removed and dipped in the carrier liquid and manually rotated clockwise and counterclockwise, followed by pressing the swab against the side of the vial containing the carrier liquid above the surface of the liquid to release additional material.

Carrier liquid containing the samples prepared above was then further processed essentially as described in US2013/0209992 (incorporated herein by reference for all purposes), including target capture with nonspecific poly-(k) capture oligomers, to obtain nucleic acid suitable for amplification and detection.

An INVADER PLUS invasive cleavage assay targeting the *C. difficile* Toxin A and B genes, tcdA and tcdB. was performed on each sample with an oligomer set comprising amplification oligomers including i-primers, primary probes, and a FRET cassette that detects either the tcdA or tcdB cleaved probes. Detection results, expressed as threshold cycle (Ct), are shown below. Results are also shown as colony forming units (CFU) per reaction, which were determined using a standard curve.

TABLE 1

Results for processing by pipet, primary swab, or secondary swab transfer.

| Sample | Type of processing | INVADER PLUS replicate results (Ct) | | | Mean Ct | CFU replicate results | | | Mean CFU |
|---|---|---|---|---|---|---|---|---|---|
| 1 | Pipet | 29.96 | 32.74 | 32.16 | 31.62 | 1.54 | 0.14 | 0.23 | 0.64 |
|  | Primary swab | 28.44 | 28.20 | 27.91 | 28.18 | 5.68 | 7.01 | 8.93 | 7.21 |
|  | Secondary swab | 32.17 | 32.98 | 32.06 | 32.40 | 0.23 | 0.11 | 0.25 | 0.20 |
| 2 | Pipet | 23.75 | 23.70 | 23.75 | 23.73 | 319 | 334 | 321 | 324.67 |
|  | Primary swab | 20.91 | 21.02 | 20.98 | 20.97 | 3653 | 3340 | 3464 | 3485.67 |
|  | Secondary swab | 23.74 | 23.20 | 23.13 | 23.36 | 322 | 515 | 545 | 460.67 |
| 3 | Pipet | 24.99 | 25.34 | 25.33 | 25.22 | 110 | 82 | 82 | 91.33 |
|  | Primary swab | 23.48 | 23.63 | 23.81 | 23.64 | 405 | 354 | 305 | 354.67 |

TABLE 1-continued

Results for processing by pipet, primary swab, or secondary swab transfer.

| Sample | Type of processing | INVADER PLUS replicate results (Ct) | | | Mean Ct | CFU replicate results | | | Mean CFU |
|---|---|---|---|---|---|---|---|---|---|
| | Secondary swab | 25.76 | 26.85 | 25.00 | 25.87 | 57 | 22 | 109 | 62.67 |
| 4 | Pipet | 21.79 | 21.91 | 21.82 | 21.84 | 1716 | 1553 | 1677 | 1648.67 |
| | Primary swab | 21.01 | 20.97 | 21.02 | 21.00 | 3373 | 3492 | 3327 | 3397.33 |
| | Secondary swab | 21.79 | 21.79 | 21.67 | 21.75 | 1717 | 1717 | 1913 | 1782.33 |

The results indicate that the primary swab approach most efficiently transferred detectable *C. difficile* material into the carrier liquid. Without wishing to be bound by theory, a potential interpretation of the results may be that during the primary swab process, some cells become firmly attached to the swab and do not elute off but do undergo lysis, releasing their DNA into the carrier liquid; the DNA from these firmly attached cells contributes to the reaction for the primary swab approach but not in the other two reaction conditions.

Firmly attaching analyte (e.g., cells or macromolecules) to the swab can be beneficial in that the firmly attached cells are effectively purified by the release of less firmly attached material into the wash liquid, and/or upon lysis or other processing such as treatment with detergent and/or salt, the firmly attached analyte contributes to increasing the amount of analyte released into the carrier liquid and its ratio to impurities. The use of a swab to preferentially hold cells or macromolecules to facilitate their isolation from impurities such as particulate matter and/or viscous polymers differs from conventional sample processing methods in which procedures such as pipetting, filtration, etc. are used in that does not rely on the flow of a liquid, which is necessary for such conventional methods (e.g., to transfer a sample via pipet and/or isolate a filtrate from a retentate).

What is claimed is:

1. A method of processing a biological sample, the method comprising:
   a. transferring a primary swab associated with an aliquot of the biological sample into a wash liquid contained in a first vessel, wherein a first portion of the aliquot is released into the wash liquid; and
   b. transferring the primary swab into a carrier liquid separate from the wash liquid, wherein the carrier liquid is contained in a second vessel, wherein a second portion of the aliquot is released into the carrier liquid to provide a quantity of target analyte for analytical processing.

2. The method of claim 1, wherein the biological sample is a suspension.

3. The method of claim 1, wherein the biological sample comprises particulate matter, at least one viscous polymer, and/or a lipid.

4. The method of claim 3, wherein the first portion of the aliquot released into the wash liquid comprises a greater amount of particulate matter than does the second portion; the first portion of the aliquot comprises a greater amount of the at least one viscous polymer than does the second portion; the at least one viscous polymer includes a polysaccharide and/or extracellular nucleic acid; and/or the biological sample comprises a lipid phase or a lipid emulsion.

5. The method of claim 1, wherein the biological sample comprises stool.

6. The method of claim 1, wherein the biological sample comprises sputum, mucus, blood, soil, sludge, or a microbial growth.

7. The method of claim 1, wherein the biological sample is of plant or animal origin, or is obtained from a food.

8. The method of claim 1, wherein the primary swab undergoes agitation in at least one of the wash liquid or the carrier liquid to facilitate release of the first and/or second portion of the aliquot from the primary swab.

9. The method of claim 8, wherein the agitation in the wash liquid further comprises swirling, stirring, or rotating the primary swab in the wash liquid and pressing the primary swab against a wall of the first vessel during at least part of the swirling, stirring, or rotating.

10. The method of claim 1, wherein the primary swab comprises a tip and the tip comprises flocked fibers or wrapped fibers.

11. The method of claim 1, wherein the biological sample comprises or is suspected of comprising a *Clostridium*, a *Staphylococcus*, a gastrointestinal pathogen, a norovirus, a *Campylobacter*, a *Plesiomonas*, a *Salmonella*, a *Vibrio*, a *Yersinia*, an *E. coli*, a *Shigella*, a *Cryptosporidium*, a *Cyclospora*, an *Entamoeba*, an Adenovirus, a Rotavirus, or a Sapovirus.

12. The method of claim 1, wherein the carrier liquid comprises one or more of a protease, an RNase inhibitor, an RNase, or a divalent cation chelator, and/or wherein the carrier liquid is a lysis solution; or wherein the method further comprises adding a lysis solution to the carrier liquid after step (b); or wherein the biological sample comprises cells and the method further comprises lysing cells after step (b).

13. The method of claim 1, wherein the biological sample comprises at least one target nucleic acid, and the method further comprises capturing the target nucleic acid with at least one capture probe or isolating the target nucleic acid by precipitation or chromatography.

14. The method of claim 13, wherein the at least one capture probe includes at least one non-specific capture probe.

15. The method of claim 1, further comprising determining whether at least one macromolecule is present in the second portion of the biological sample.

16. The method of claim 1, further comprising quantifying at least one macromolecule in the second portion of the biological sample.

17. The method of claim 1, further comprising amplifying at least one nucleic acid from the second portion of the aliquot, sequencing at least one nucleic acid from the second portion of the aliquot or an amplicon thereof, and/or hybridizing a detection probe to at least one nucleic acid from the second portion of the biological sample or an amplicon thereof.

18. The method of claim 1, wherein the first portion of the aliquot released into the wash liquid comprises cells, and the method further comprises culturing cells that were released into the wash liquid or performing an optical analytical technique on cells that were released into the wash liquid.

19. The method of claim 3, wherein the first portion of the aliquot released into the wash liquid comprises a greater amount of particulate matter and/or the at least one viscous polymer than does the second portion; and the second portion of the aliquot released into the carrier liquid contains a greater quantity of the target analyte for analytical processing than does the first portion.

20. A method of processing a biological sample, the method consisting essentially of:

a. contacting a biological sample with a primary swab wherein an aliquot of the biological sample becomes associated with the primary swab;
b. transferring the primary swab associated with the aliquot into a wash liquid contained in a first vessel, wherein a first portion of the aliquot is released into the wash liquid;
c. transferring the primary swab into a carrier liquid separate from the wash liquid, wherein the carrier liquid is contained in a second vessel, wherein a second portion of the aliquot is released into the carrier liquid to provide a target analyte for processing;
d. optionally, further isolating or purifying the target analyte provided by step (c) to provide a processed target analyte; and
e. analyzing the target analyte or processed target analyte provided by step (c) and/or step (d).

* * * * *